United States Patent [19]

Thomas

[11] Patent Number: 4,609,084
[45] Date of Patent: * Sep. 2, 1986

[54] TRAVEL PACK

[76] Inventor: Frank O. Thomas, 5167 S. 600 East, Murray, Utah 84107

[*] Notice: The portion of the term of this patent subsequent to Apr. 30, 2002 has been disclaimed.

[21] Appl. No.: 728,250

[22] Filed: Apr. 29, 1985

Related U.S. Application Data

[63] Continuation-in-part of Ser. No. 428,103, Sep. 29, 1982, Pat. No. 4,513,866.

[51] Int. Cl.⁴ .............................................. A45C 11/00
[52] U.S. Cl. .................................... 190/110; 190/111; 206/549; 224/32 R; 224/259
[58] Field of Search ............................ 150/52 J, 52 R; 190/102, 106, 109–111, 122; 206/372, 373, 376, 459; 224/151, 153, 209, 215, 30 R, 32 R, 259

[56] References Cited

U.S. PATENT DOCUMENTS

| | | | |
|---|---|---|---|
| D. 230,327 | 2/1974 | Cooperstein | D87/5 G |
| D. 231,868 | 6/1974 | Ohyama | D87/5 G |
| 1,705,149 | 3/1929 | Brady | 190/43 |
| 2,324,194 | 7/1943 | Campiglia | 224/5 |
| 3,019,952 | 2/1962 | Brewster | 224/9 |
| 3,622,056 | 11/1971 | Droeger | 224/9 |
| 3,759,356 | 9/1973 | Bostick et al. | 190/42 |
| 3,926,234 | 12/1975 | Dean | 150/40 |
| 4,169,550 | 10/1979 | Williams | 224/211 |
| 4,236,657 | 12/1980 | Brunton | 224/153 |
| 4,241,833 | 12/1980 | Luebcke | 206/570 |
| 4,342,390 | 8/1982 | Mitchell et al. | 206/363 |
| 4,386,642 | 6/1983 | Durbin | 150/34 |
| 4,402,439 | 9/1983 | Brown | 224/30 R |

Primary Examiner—William Price
Assistant Examiner—Jimmy G. Foster
Attorney, Agent, or Firm—Workman, Nydegger & Jensen

[57] ABSTRACT

A travel pack for storing and transporting equipment, clothing, food, or other supplies is provided with a lid which has operable positions of at least a closed position, a half-open position, and a fully opened position. Pockets are provided in the pack to hold various items and are arranged such that all of the contents can be accessed in confined spaces when the pack is in the half-open position, as well as when it is in the fully open position. Unique open drawer pockets are located within the pack and are accessible either through the open ends or by opening the top flaps.

27 Claims, 14 Drawing Figures

TRAVEL PACK

RELATED APPLICATIONS

This application for Letters Patent is a continuation-in-part of applicant's copending application entitled "Emergency Medical Pack," Ser. No. 428,103, filed Sept. 29, 1982, now U.S. Pat. No. 4,513,866 issued Apr. 30, 1985. The aforesaid patent application is incorporated herein by this reference.

BACKGROUND

1. The Field of the Invention

The present invention relates to readily transportable packs, bags, and other types of luggage used in handling and storing numerous, independent components of equipment, supplies, or clothing. More particularly, this invention is directed to a portable pack or other type of luggage wherein all of the stored components are readily and independently accessible, even when the pack is located in a confined area.

2. The Prior Art

Numerous types of luggage, backpacks, and other types of travel bags are, of course, well known in the art. For example, many types of conventional suitcases are available. Most suitcases, however, must be folded open so that when the suitcase is open it occupies approximately twice as much surface area as it does when it is closed. Similarly, this is also often true of other types of luggage and travel bags.

One of the major problems which is increasingly encountered in crowded aircraft and other confined areas is the necessity of accessing the interior of a bag or other piece of luggage in a confined space. Because of the small amount of the space available in a crowded aircraft or bus, or even in a closet, access to suitcases is often extremely limited or unavailable since it is unlikely that there will be sufficient space available to fully unfold a suitcase.

Access to specific needed items located within the suitcase is often very restricted in such areas of confinement. Frequently, conventional packs permit access to their contents through a single opening in one portion of the body of the pack. In the use of packs having only a single opening for access, it would be appreciated that rapid identification of desired items from deep within the pack can be extremely difficult and a frustration task. Likewise, for the reasons mentioned above it is generally difficult to open a suitcase in a confined area sufficiently to readily identify all of the contents.

Another problem which is often encountered in the use of conventional luggage is the inability to separate various items stored within the luggage. For example, most conventional suitcases provide few, if any, separate compartments for storing different types of clothing. As a result, it is not unusual for a traveler's toiletries to become mixed with his clothing, and for various types of clothing to become intermixed. This problem is further complicated when the pack or luggage must carry food items, cooking utensils, and similar supplies. Intermixing of such items can result in soiled clothing and damaged supplies.

Prior art packs and luggage rarely provided a method for easily unpacking or for carrying certain items to locations remote from the luggage. For example, it may be desirable to easily remove all of one's socks, shirts, or athletic equipment and place them in appropriate locations in a hotel room. Similarly, when backpacking it may be desirable to carry certain cooking utensils to another part of a camp. These needs have not been adequately met in the prior art.

Accordingly, it would be a significant advancement in the art to provide a travel pack which could carry various types of equipment, clothing, or food in segregated compartments.

It would be a still further advancement in the art if some of the contents of the bag could be transported to a location remote from the bag itself. It would be a further advancement in the art if the entire contents of the pack were readily accessible and identifiable, even in confined areas. It would also be an advancement in the art to provide a travel pack wherein various pieces of equipment, clothing, and supplies could be removed in separate pouches. Such apparatus are described and claimed herein.

BRIEF SUMMARY AND OBJECTS OF THE INVENTION

The present invention relates to a novel travel pack or bag used to transport equipment, supplies, clothing, and other items. The bag includes a number of pockets which hold, protect, and allow rapid access to the contents of the pack as needed. The pack is configured to be easily transported by a person travelling on foot, and to provide rapid access to its contents during use in confined areas, such as while travelling on an aircraft or bus.

The travel pack preferably has a generally rectangular box shape with the front portion having a lid which is preferably zippered on three sides to provide ready access to the interior contents. The lid is designed such that it can be positioned in a closed position, a half open position, or fully opened position. The travel pack can be carried by hand utilizing handles located on the top of the pack, worn as a backpack if it must be carried for greater distances or if the user needs to have both hands free, or can be mounted on a bicycle or motorcycle.

The design of the pack is such that the lid can be unzipped half way and folded back on itself in a "half open" configuration while still permitting ready access to all of the contents of the bag. Of particular significance is the fact that all of the contents of the bag can be readily accessed when the lid is in the half open position, as well as when the lid is in the fully opened position. Thus, the entire contents of the bag can be accesed while the lid is only half open. This is significant because it is often difficult or impossible to fully open the prior art packs or luggage so as to access all of their contents while in areas of confinement.

Pockets are located in the body of the pack as well as in the lid and on the sides of the pack to hold and protect the contents of the pack. Specially designed pockets, referred to as "open drawer pockets," are located in the bottom portion of the body of the pack. These pockets can either be accessed through an open end located at about the mid line of the pack, if the pack is in the half opened or fully opened position, or they can be accessed from above by opening the pocket along its length if the pack is in the fully opened position. Located within these open drawer pockets are separate pouches containing desired items. These pouches facilitate removal of various items from the pack and also allow those items to be carried to another location without moving the entire pack.

It is, therefore, a primary object of this invention to provide a travel pack wherein all of the contents can be readily identified and accessed even in confined areas.

It is a related object of the present invention to provide a travel pack wherein all of the contents can be accessed while the pack is in the half-open position.

Another objection of the present invention is to provide a travel pack which occupies the same amount of surface area when the pack is in the half-open position as it does when the pack is in the closed position.

It is a further object of this invention to provide a travel pack which provides protection, storage, and rapid accessibility of groups of items, equipment, clothing or supplies, which in turn can be easily transported to a location remote from the pack.

These and other object and features of the present invention will become more fully apparent from the following desription and appended claims taken in conjunction with the accompanying drawings.

DETAILED DESCRIPTION OF THE PREFERRED EMBODIMENTS

The present invention is best understood with reference to the Figures wherein like numerals designate like parts throughout. The travel pack 10 of the present invention is illustrated from the front and rear and in the closed configuration in FIGS. 1 and 3.

Figures 1, 3:
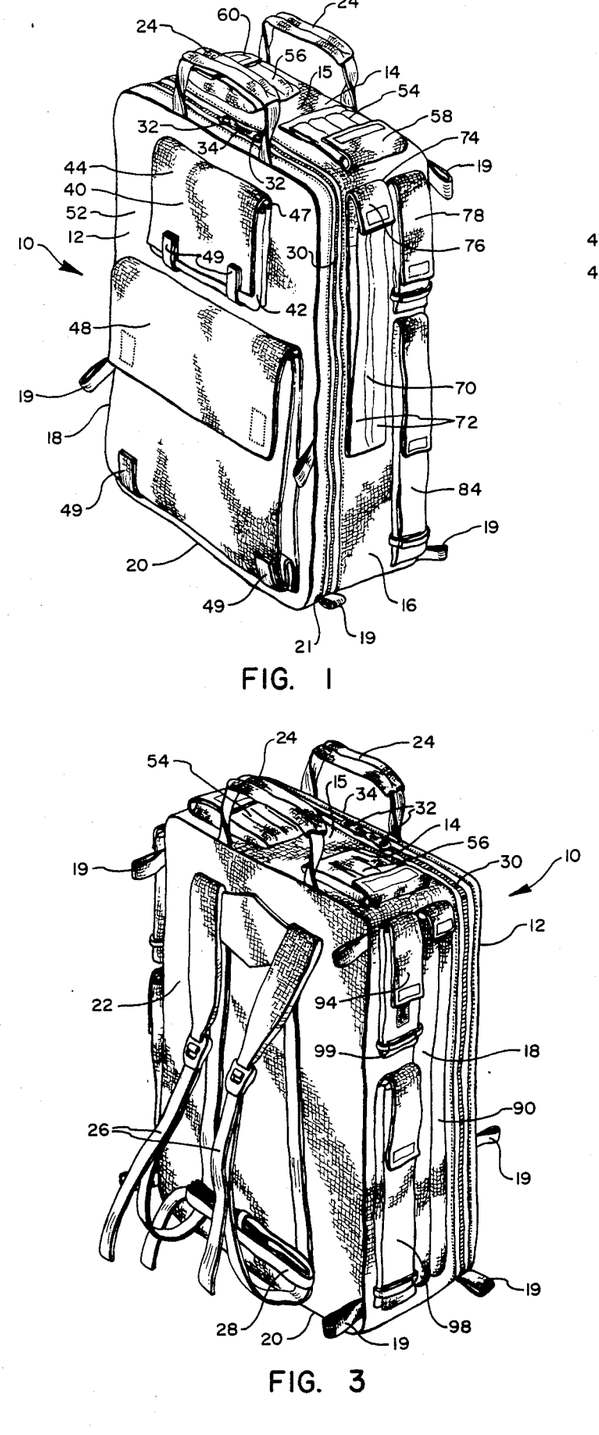
FIG. 1 is a front perspective view of a travel pack of the present invention as is standing upright in the closed position.
FIG. 3 is a rear perspective view of a travel pack of the present invention as it is standing upright in the closed position.

The front 12 of the travel pack 10, is illustrated in FIG. 1, and is generally rectangular in shape. Pack 10 further comprises a top 14, a right side 16, a left side 18, a bottom 20, and a back 22. Handles 24 are attached to front 12 adjacent top 14, and to back 22 adjacent top 14. Handles 24 allow pack 10 to be hand carried for a short distances.

As illustrated in FIG. 3, optional shoulder straps 26 and belt strap 28 are provided which are attached to back 22 of pack 10 so that pack 10 may be worn as a backpack. This is important if pack 10 must be carried a great distance of if the carrier needs both hands free while carrying the pack. Also included on pack 10 are stablizing loops 19. Loops 19 are included so that pack 10 can be tied down to prevent it from sliding while being transported or stored.

Figure 6:
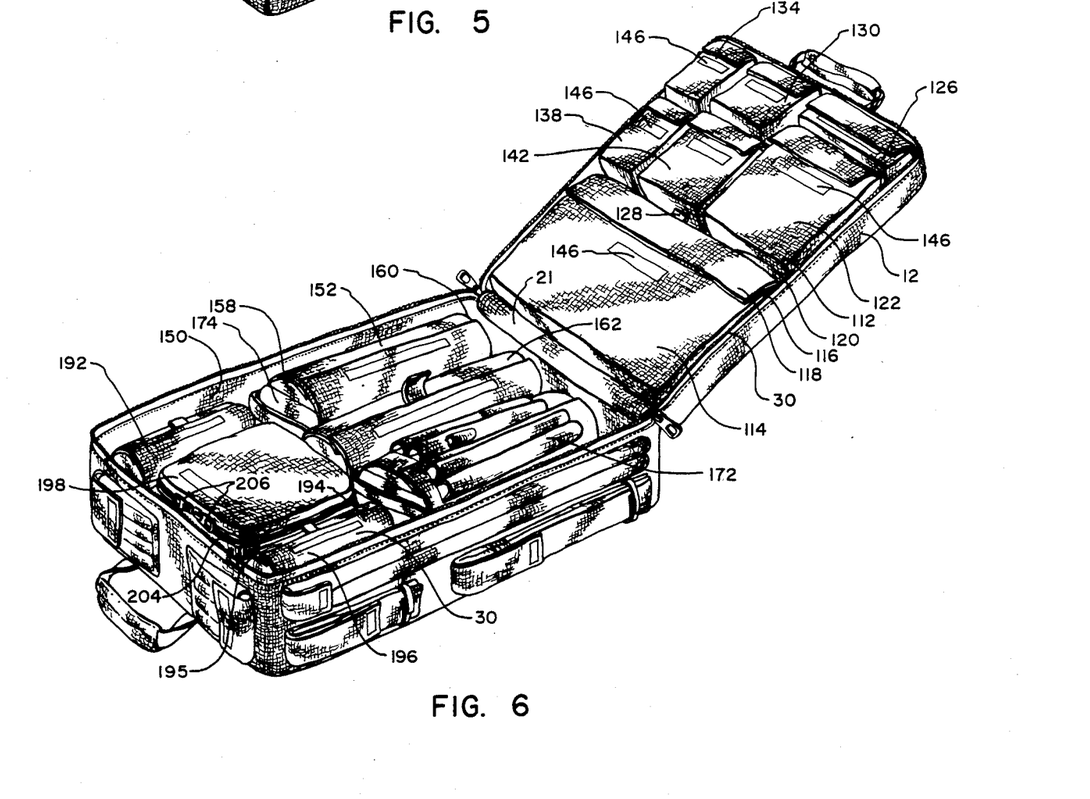
FIG. 6 is a perspective view of a travel pack of the present invention, in the fully opened position illustrating the interior pockets of the pack.

As illustrated in FIGS. 1 and 6, front 12 is hingedly connected to bottom 20 along edge 21. A zipper 30 extends along the remaining three sides of front 12 and along sides 16 and 18 and top 14 of pack 10 period. Zipper 30 attaches front 12 to top 14 and sides 16 and 18 when pack 10 is in the closed position.

In the preferred embodiment, zipper 30 is one continuous piece and has two slides 32 for opening and closing the zipper. When pack 10 is in the closed position, slides 32 meet at approximately the center 34 of top 14. Alternatively, zipper 30 could be comprised of two separate zippers, one on each side of the pack, extending from center 34 to the bottom of the respective sides. Additionally, it will be appreciated that other means could be used to close the pack.

Figure 2:
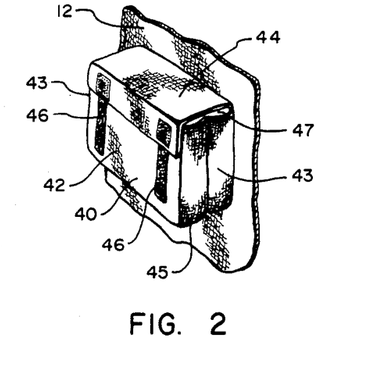
FIG. 2 is a perspective view of an external pocket in its expanded position, which pocket is attached to a travel pack of the present invention.

Pack 10 is equipped with numerous internal and external pockets to hold various items stored within the pack. Illustrated in FIG. 1 are exterior pockets 40 and 48 which are located on exterior surface 52 of front 12. The pocket 40 comprises a body 42, which is attached along three edges thereof to front 12, and flap 44. Flap 44 is attached along one edge to front 12 and is secured over the opening 47 in the top of pocket 40 by fasteners 46 (as illustrated in FIG. 2) which anchor it to body 42. In the preferred embodiment, fasteners 46 comprise strips of fabric onto which hook and loop fasteners, commonly referred to by the trademark Velcro, are attached. Pocket 40 is shown in FIG. 1 in the collapsed position.

FIG. 2 illustrates pocket 40 in the expanded position. Sides 43 and bottom 45 of pocket 40 are pleated such that pocket 40 can expand to hold equipment of different sizes. Fasteners 46 and 49, as illustrated in FIG. 1, are attached to the top and bottom of pocket 40 to prevent the top and bottom from extending outwardly when only small or thin items are stored within pocket 40. Fasteners 49 are straps of material fastened at one end to front 12 and are looped over the bottom of pocket 40 and are secured with Velcro attached to the other end.

Returning again to FIG. 1, pocket 48 is located below pocket 40 on front 12 and is similar in construction to pocket 40, except that it is larger.

Slotted pockets 54 and 56 are shown located on exterior surface 15 of top 14. Pockets 54 and 56 are attached to top 14 by a suitable means such as by sewing. In the illustrated embodiment, pocket 54 is divided into four longitudinal slots running the length thereof and pocket 56 is divided into three longitudinal slots. These slots are designed to hold various types of items which may be long and thin, such as pens, pencils, and other types of writing implements. Flaps 58 and 60 cover the open ends of pockets 54 and 56, respectively, to prevent the contents from falling out and may be fastened by the use of Velcro.

As illustrated in FIGS. 1 and 3, the exterior surface of sides 14 and 18 are also equippd with pockets. Side 16 has a slotted pocket 70 running along a substantial length thereof. In the illustrated embodiment, pocket 70 has two longitudinal slots 72 which may be designed to hold various types of specialized types of equipment such as tubing or other similarly shaped items. Openings 74 are located in the top of slot 72 to provide access to the equipment stored therein. Flap 76 covers opening 74 to prevent equipment from falling out and to prevent dirt and other foreign material from entering the pockets. Flap 76 is also secured by Velcro fasteners.

Located adjacent pocket 70 on side 16 are expandable pockets 78 and 84. These pockets are similar in construction to pockets 40 and 48 on front 12, but are considerably narrower. It will be appreciated that the precise shape and orientation of the pockets with respect to each other may vary depending on the equipment desired to be carried and stored.

Figure 4:
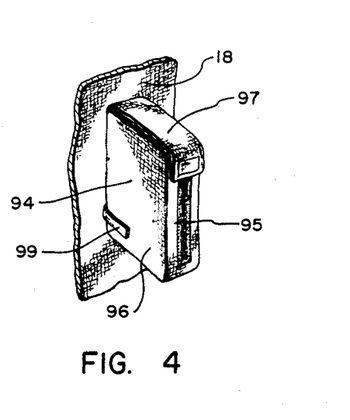
FIG. 4 is a perspective view of another external pocket in its expanded position, which pocket is attached to a travel pack.

Side 18, best illustrated in FIG. 3, also includes three exterior pockets. Slotted pocket 90 is similar to slotted pocket 70 on side 16 except that it may be longer to accommodate different sized equipment. Expandable pockets 94 and 98 are located adjacent slotted pocket 90 and are substantially identical to pockets 78 and 84. Expandable pocket 94 is illustrated in its expanded position in FIG. 4. Pocket 94 includes front 95, sides 96, and top flap 97. Flap 97 is fastened to front 95 by, for example, a Velcro closure. Strap fastener 99 is also included to hold the bottom of pocket 94 closed when the pocket is in the collapsed position and is also secured by a Velcro fastener.

Figure 5:
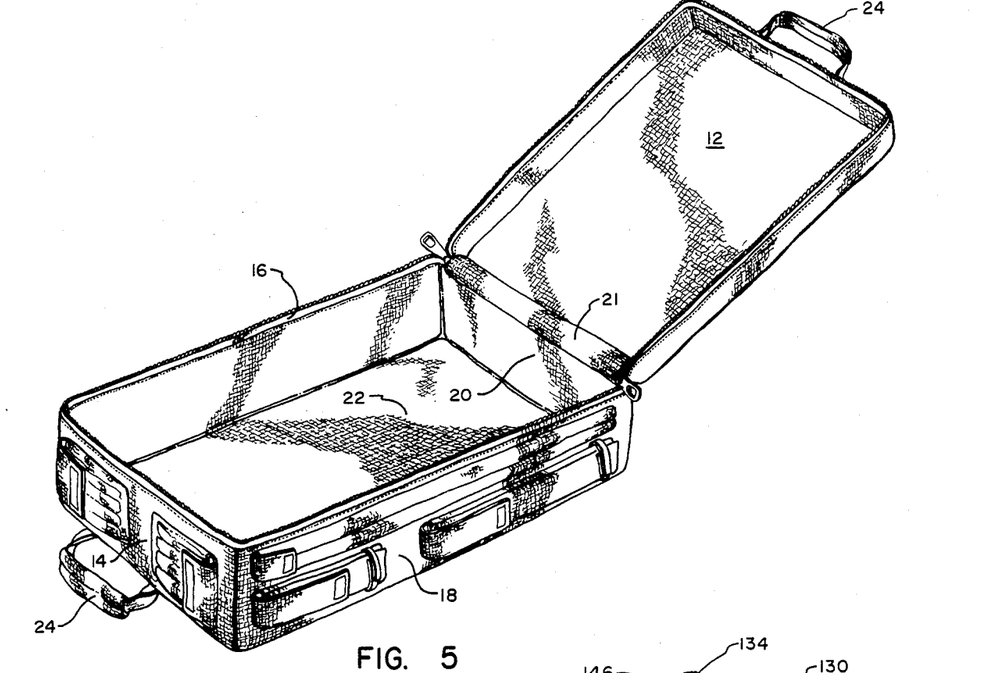
FIG. 5 is a perspective view of a travel pack of the present invention in the fully opened position wherein the pockets and the contents have been removed to illustrate the body structure of the travel pack.

FIG. 5 illustrates pack 10 in the open position without any of its internal pockets and without its contents. Front 12, top 14, sides 16 and 18, bottom 20, and back 22 can be made from nylon fabric or other similar material. It will be readily appreciated, however, that the pack 10 may also be constructed of rigid materials such as metal, plastic, or other types of durable solid material.

Figure 8:
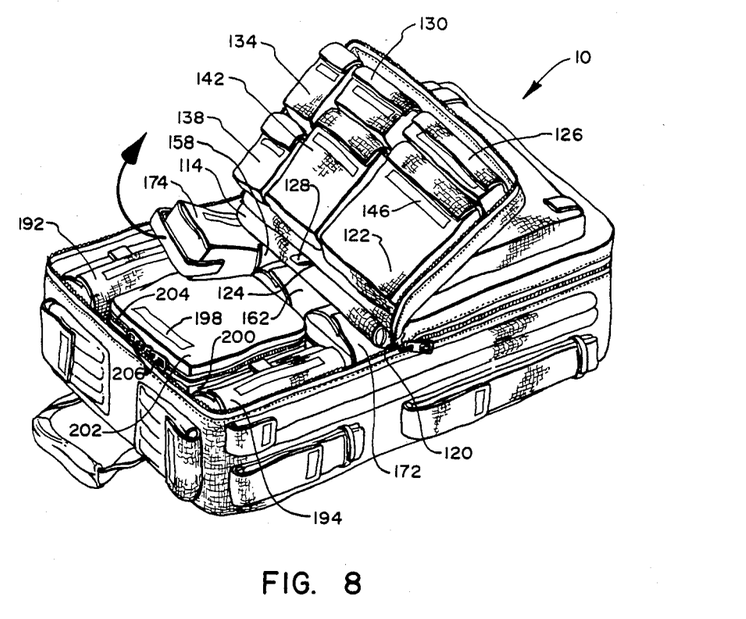
FIG. 8 is a perspective view of a travel pack in the half open position illustrating the removal of the contents from one of the open drawer pockets.

Pack 10 has two open positions as are illustrated in FIGS. 6 and 8. FIG. 6 illustrates what may be referred to as the fully opened position and FIG. 8 illustrates what may be referred to as the half open position. As will be more fully explained below, one of the major advantages of the present invention is that all of the contents of the travel pack are readily accessible when the pack is in the open position, as well as when the pack is in the fully open position.

Pack 10 is open to the half open position by pulling slides 32 to mid line 120 on each side of the pack and by rolling the upper half of front 12 back onto the lower half. It will be appreciated that in the event pack 10 is constructed of rigid material, mid line 120 may constitute a hinge or other type of mechanism over which the upper half of front 12 can be pivoted onto its lower half.

In the half open position, all of the contents of pack 10 can be accessed without increasing the surface area on which pack 10 rests. The pack is positioned in the fully opened position by moving slides 32 to the bottom of front 12 and folding the entire front back.

With continuing reference to FIGS. 6 and 8, the interior pockets of travel pack 10 are best illustrated. Attached to the interior surface 112 of front 12 are seven pockets in the illustrated embodiment. Pocket 114 is located on the lower half of front 12 and extends from sides 18 to side 16 and from mid line 120 to the bottom of front 12. Pocket 114 is attached to the interior lining of front 12 by suitable means such as by sewing.

Opening 116 of pocket 114 is located along mid line 120 such that when pack 10 is in the half open position as illustrated in FIG. 8, the contents of pocket 114 can still be accessed. Flap 118 extends along opening 116 and can be secured by Velcro fasteners or other means to securely close pocket 114.

Located above mid line 120 are interior pockets 122, 126, 130, 134, 138, and 142. These pockets are similar in configuration to pocket 114, but are all smaller in size to accommodate various types of equipment or supplies. Each of pockets 114, 122, 126, 130, 134, 138, and 142 may include a label 146 on which the name of the contents of the respective pocket can be written. Accordingly, the contents of each pocket can be determined by the size of the pocket as well as by reading the identification label.

Pockets 122, 126, 130, 134, 138, and 142 are all attached to a separate sheet of material which forms their backs. This sheet is securely attached along its top and sides to the interior lining of front 12. Thus, an additional pocket is located beneath pockets 122, 126, 130, 134, 138, and 142, which has an opening along mid line 120. Tab 128 is utilized to open the opening which is secured by Velcro fasteners.

Figure 9:
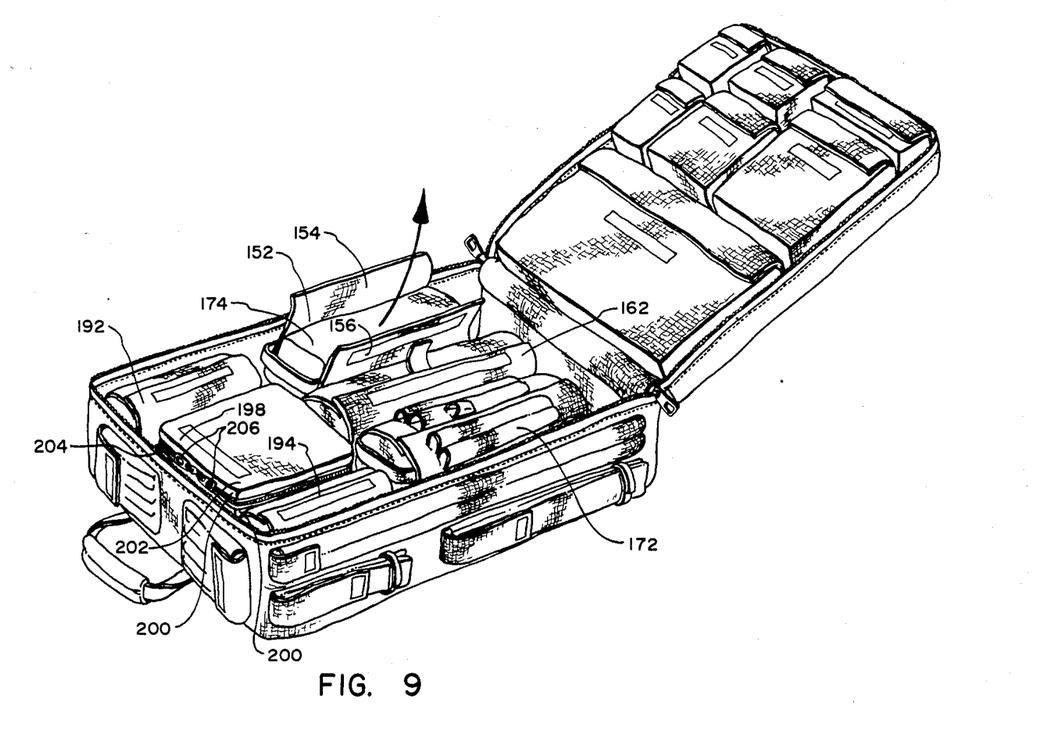
FIG. 9 is a perspective view of the travel pack in the fully opened position illustrating the removal of the contents from the open drawer pockets from the top entrance.

Referring now to FIGS. 6 and 9, located within body 150 of pack 10 are six major pockets. The three pockets 152, 162, and 172 which are located in the lower half of body 150 are referred to as lower drawer pockets. The unique design of these pockets allows the contents to be accessed when pack 10 is in either the half open or fully opened position. Each of pockets 152, 162, and 172 comprises a sheet of nylon fabric or other suitable material which is securely attached along its center to bottom 22 of pack 10. Alternatively, pockets 152, 162, and 172 could be formed from two separate sheets of material, each attached along one side to bottom 22.

Pockets 152, 162, and 172 are illustrated in their closed position in FIG. 6. Open drawer pocket 152 is illustrated in the open position in FIG. 9. Pocket 152 comprises a first side 154 and a second side 156.

The contents of pocket 152 are contained within a pouch 174 which is more fully described below. The equipment, clothing, supplies, or food contained in pouch 174 is positioned between sides 154 and 156 which are then folded over pouch 174 and are secured as illustrated in FIG. 6 by a Velcro fastener.

The ends 158 and 160 of open drawer pocket 152 are left open. Thus, pouch 174 containing the materials stored in pocket 152 can be removed either by pulling pouch 174 out of end 158, as illustrated in FIG. 8, if pack 10 is in the half open or fully opened position, or by separating sides 154 and 156 of pocket 152 as illustrated in FIG. 9 and lifting pouch 174 out if pack 10 is in the full fully opened position.

The design of open drawer pockets 152, 162, and 172 allows the contents of these pockets to be easily accessed even when the pack is only in the half-opened position. This is a significant benefit when the travel pack is used in various areas of limited space.

Open draweer pockets 152, 162, and 172 may contain various types of individual equipment, clothing, food or other types of supplies. These items are packed in pouches such as pouch 174 illustrated in FIG. 10, to facilitate their removal and to also allow the contents to be easily carried to a location remote from the travel pack. This allows an individual to remove only the desired items from the travel pack and to place those items in specific locations. For example, it may be possible to pack toiletries in one of open drawer pockets 152, 162, or 172 and then to remove such a pouch to a desired location in a hotel room or other place of lodging.

Figure 7:
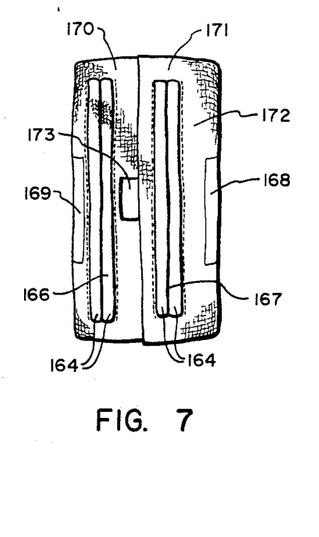
FIG. 7 is a top view of an open drawer pocket of the present invention illustrating the small additional pockets which are located on the top and sides thereof.

Open drawer pocket 172 is shown in greater detail in the closed position in FIG. 7. Pocket 172 comprises sides 170 and 171 which are sealing closed with Velcro fasteners and are opened by pulling on tab 173. Slot pockets 166 and 167 are located on flaps 170 and 171 respectively. Slot pockets 166 and 167 are sewn onto flaps 170 and 171 and have elasticized open ends 164. These pockets may be configured to accommodate various types of specific equipment. Open drawer pockets 152 and 162 can also include similar slots pockets.

Located on the sides 170 and 171 of pocket 172 are straps 168 and 169. These straps are sewn to sides 170 and 171 along the edges which are parallel to the edge of the side which is connected to the pack. Accordingly, additional equipment or supplies can be slid underneath straps 168 and 169 and secured in place.

Figure 10:
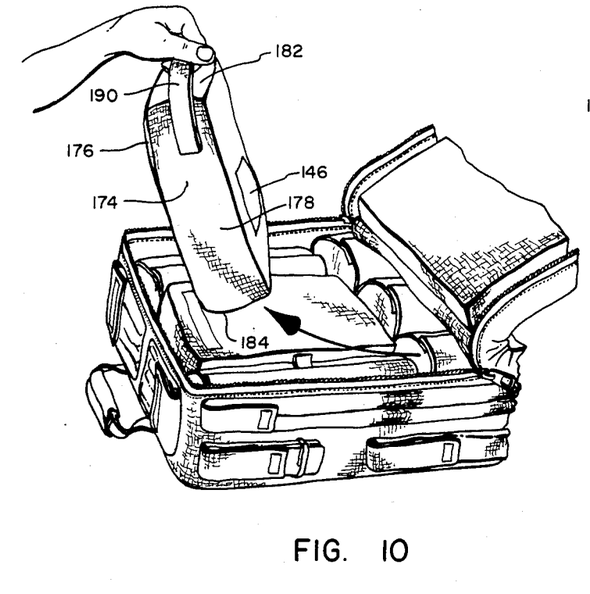
FIG. 10 is a perspective view of a portion of the travel pack in a half open position illustrating an internal pouch after it has been removed from one of the open drawer pockets.
Figure 11:
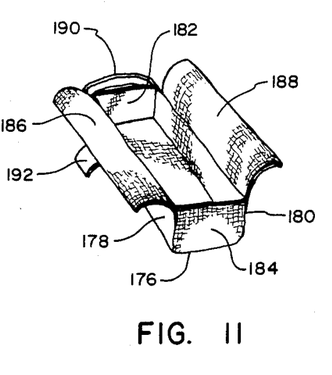
FIG. 11 is a perspective view of a pouch illustrating its configuration.

Pouch 174 is illustrated in greater detail in FIGS. 10 and 11. Pouch 174 is generally box like in configuration having a bottom 176, sides 178 and 180, top end 182, bottom end 184, cover flaps and 186 and 188 and a strap 190. The supplies, clothing or other types of equipment are placed within pouch 174 and cover flaps 186 and 188 are folded over the top and secured by Velcro fasteners. Pouch 174 can be placed between sides 154 and 156 of pocket 152 and secured in place.

Pouch 174 is removed from the open drawer pocket either by grasping strap 190 and pulling the pouch out the open end or by opening flaps 154 and 156, and lifting the pouch out. Contents of pouch 174 can then be removed by opening flaps 186 and 188 by pulling on tab 192. Alternatively, the contents of pouch 174 can be accesed if pack 10 is in the fully open position by opening sides 154 and 156 and flaps 186 and 188, and by directly removing the contents. A label 146 can also be included on pouch 174 to identify its contents.

Referring again to FIGS. 6, 8, and 9, also located within body 150 of pack 10 are pockets 192, 194, and 198. Pockets 192 and 194 are similar in construction to open drawer pockets 152, 162, and 172 in that they are formed from two sheets of material which are sewn along one edge to the interior surface of back 22 of pack 10. Pocket 194 is formed from sheets 195 and 196 which are folded over the equipment stored therein and are secured by Velcro fasteners. Pocket 194 is identical to pocket 194, but it is located adjacent the other side of pack 10.

Pocket 198 is essentially square shaped and is located between pockets 192 and 194. The base of pocket 198 if formed by a portion of back 22. Four sides walls 200 are attached to back 22 to form a box-like configuration. Lid 202 is permanently attached to one of side walls 200. A zipper 204 having two slides 206 is attached to the remaining three sides walls 200 and the remaining three edges of lid 202. Zipper 204 is used to sealingly close pocket 198.

Figure 12:
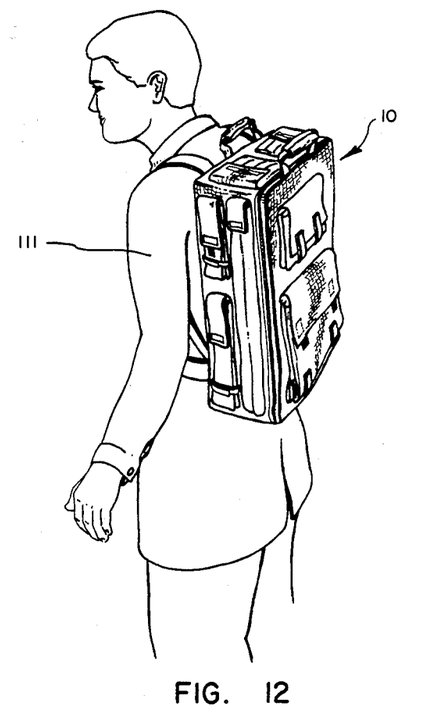
FIG. 12 is a perspective view of a person wearing the travel pack on his back in the closed position.
Figure 13:
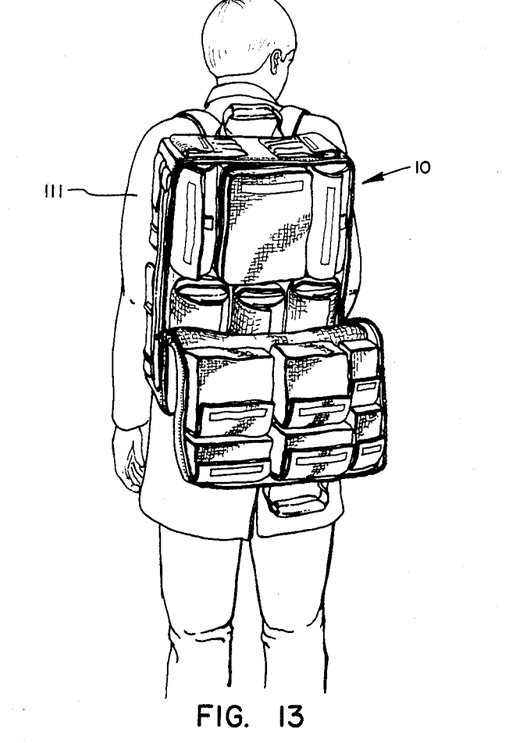
FIG. 13 is a perspective view of a person wearing the travel pack on his back in the half open position wherein an associate can have access to all of the contents of the pack.

As illustrated in FIGS. 12 and 13, pack 10 can be worn on the back of a person 111, thus freeing his hands to perform other tasks. FIG. 12 illustrates pack 10 in the closed position such as during transit. FIG. 13 shows pack 10 in the half open position such that a second person can access all of the contents of travel pack 10 without opening the pack 10 to such an extent that it becomes awkward and burdensome to the person carrying it.

Figure 14:
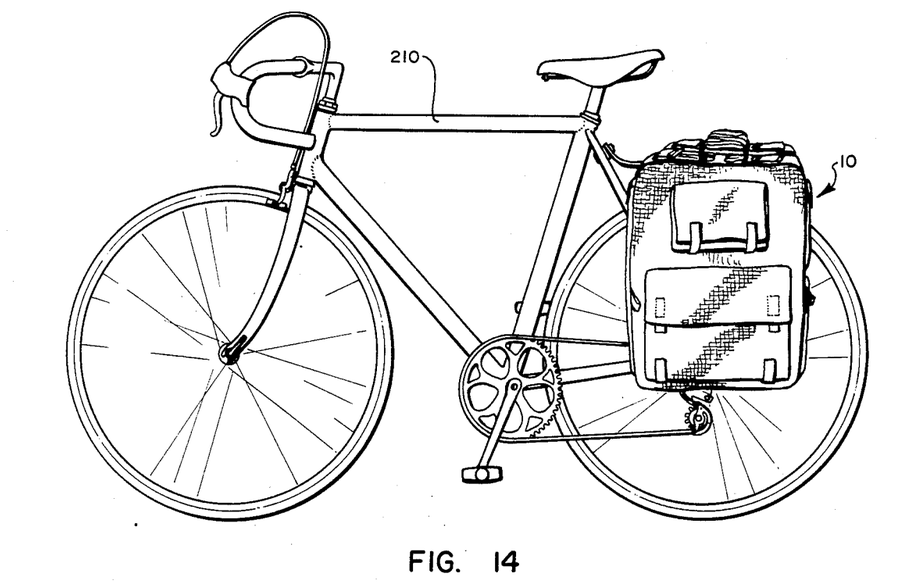
FIG. 14 illustrates the travel pack mounted on a bicycle.

FIG. 14 illustrates pack 10 mounted to the rear of a bicycle 210. Thus, the pack 10 is easily transported and used by bicyclists and motorcyclists.

The split back lid which allows all of the contents of the pack to be accessed when the pack is in the half open as well as the fully open position is a significant improvement over prior art packs. The pack can be accessed by a second person while the bearer still has it on his back. More importantly, the contents of the pack can be accessed in confined spaces such as on aircraft, buses and in other close locations.

It will be appreciated that the arrangement and size of the various pockets can be varied to accommodate specific needs. Also, the specific design might be altered for specific uses.

As will be readily appreciated, the invention may be embodied in other specific forms without departing from the spirit or central characteristics. The described embodiments are to be considered in all respects only as illustrative and not restrictive. The scope of the invention is, therefore, indicated by the appended claims rather than by the foregoing description. All modifications or changes which come within the meaning and range of equivalency of the claims are to be embraced within their scope.

What is claimed and desired to be secured by U.S. Letters Patent is:

1. A travel pack comprising:
    a body having a generally planar back with a plurality of sides extending upwardly from the peripheral edges of said back;
    lid means forming a front on the back, said lid means being attached along a portion of one end thereof to at least one of the sides of the body, and the lid means being configured so as to provide a plurality of operable positions, each permitting user access to substantially all materials contained within the pack;
    a connecting means for detachably securing the lid means along its remaining edges to the sides of the pack; and
    at least one drawer pocket means located in the pack, each of said drawer pocket means securing a pouch within the pack, each drawer pocket means being formed as a receptacle for the respective pouch with at least one side of each drawer pocket means being capable of being opened such that the pouch is removable from the drawer pocket means, the pouch having a handle mounted to one end thereof for use in removing the pouch from the drawer pocket means, the pouch providing storage such that the items stored in the pouch are accessible by opening the drawer pocket means when the pouch remains within the pack, at least one of the drawer pocket means attached to the body having an opening substantially adjacent to the foldable position of the lid means so as to permit user access into that drawer pocket means when the lid means is in the partially open position, all of the drawer pockets means being oriented in the same direction within the pack when the pack is completely closed such that the contents of all of the drawer pocket means are accessible when the pack is in either the fully open or the partially open position.

2. A travel pack as defined in claim 1 wherein the drawer pocket means comprise drawer pockets and wherein the pack comprises at least two drawer pockets.

3. A travel pack as defined in claim 2 wherein said pouches within the drawer pockets can be readily removed from the drawer pockets without releasing the drawer pocket means which secures the pouches.

4. A travel pack as defined in claim 1 wherein the connecting means comprises a zipper.

5. A travel pack as defined in claim 1 further comprising means for transporting said pack.

6. A travel pack as defined in claim 5 wherein the transporting means comprises handles whereby the pack can be carried by hand.

7. A travel pack as defined in claim 5 wherein the transporting means comprises shoulder straps such that the pack can be worn by a carrier on his back.

8. A travel pack as defined in claim 1 further comprising pockets attached to at least one exterior surface of the pack.

9. A travel pack as defined in claim 1 wherein the transporting means comprises means for attaching the pack to a bicycle.

10. A travel pack comprising:
a body having a generally planar back with a least three sides extending upwardly from the peripheral edges of the back;
lid means forming a front on the pack, said lid means being attached along a portion of one end thereof to one of the sides of the body, the lid means being configured so as to have operable positions of at least a closed position and a partially open position, the lid means being foldable at at least one position along its width so as to place it in the partially open position, the pack occupying substantially the same amount of surface space when the lid is in the partially open position as when the lid is in the closed position and user access to substantially all materials within the pack being permitted when the lid is in the partially open position;
a connecting means for detachably securing the lid means along its remaining edges to the sides of the pack; and
a plurality of pockets for securing and organizing items stored in the pack, at least one of the pockets being attached to the lid means and at least one of the pockets being attached to the body, at least one of the pockets attached to said body having an opening substantially adjacent to the foldable position of the lid means so as to permit user access into that pocket when the lid means is in the partially open position, all of the pockets being oriented in the same direction within the pack when the pack is completely closed such that the contents of all of the packets are accessible when the pack is in either the fully open or the partially open position.

11. A travel pack as defined in claim 10 wherein at least one of the pockets comprises a drawer pocket.

12. A travel pack as defined in claim 11 wherein the pack further comprises a removable pouch located within the drawer pocket wherein the pouches are transportable to a remote location.

13. A travel pack as defined in claim 10 wherein the connecting means comprises a zipper.

14. A travel pack as defined in claim 10 further comprising means for transporting the pack.

15. A travel pack as defined in claim 14 wherein the transporting means comprises handles whereby the pack can be carried by hand.

16. A travel pack as defined in claim 14 wherein the transporting means comprises shoulder straps such that the pack can be worn by a carrier on his back.

17. A travel pack as defined in claim 10 further comprising a plurality of slotted pockets attached to at least one exterior surface of the pack.

18. A travel pack comprising:
a body;
a split-back lid being configured so as to have operable positions of at least a closed position, a partially open position, and a fully open position, said lid being foldable at at least one position along its width so as to place it in the partially open position, the pack occupying substantially the same amount of surface space when the lid is in the partially open position as when the lid is in the closed position and user access to substantially all materials within the pack being permitted when the lid is in the partially open position;
at least two drawer pockets located within the interior of the pack for securing and organizing equipment stored in said pack, at least one of the drawer pockets being attached to the lid and at least one of the drawer pockets being attached to the body, at least one of the drawer pockets attached to the body having an opening substantially adjacent to the foldable position of the lid so as to permit user access into that drawer pocket when the lid is in the partially open position, all of the drawer pockets being oriented in the same direction within the pack when the pack is completely closed such that the contents of all of the drawer pockets are accessible when the pack is in either the fully open or the partially open position, each drawer pocket comprising:
a first side generally rectangular in shape and being securely attached along one edge thereof to the body;
a second side generally rectangular in shape and being securely attached along one edge thereof to the body in a position substantially parallel to the first side;
fastening means along a distal edge of both the first and the second parallel sides, said fastening means being designed so as to secure the distal edge of the first side to the distal edge of the second side.

19. A travel pack as defined in claim 18 wherein the first and said second sides of the open drawer pocket are formed from a single sheet of material which is fastened along a center portion thereof to the pack.

20. A travel pack as defined in claim 18 wherein the first and the second sides of the open drawer pocket are formed from separate sheets of material.

21. A travel pack as defined in claim 18 further comprising a pouch means for holding equipment, the pouch means being positioned within at least one of said open drawer pockets.

22. A travel pack as defined in claim 18 further comprising labels on an exterior surface of each open drawer pocket for identifying the contents of the pocket.

23. A travel pack as defined in claim 18 further comprising means for transporting the pack.

24. A travel pack as defined in claim 23 wherein the transporting means comprises handles whereby the pack can be carried by hand.

25. A travel pack as defined in claim 23 wherein the transporting means comprises shoulder straps such that the pack can be worn by a carrier on his back.

26. A travel pack as defined in claim 23 wherein the transporting means comprises means for attaching the pack to a bicycle.

27. A travel pack comprising:
- a body having a generally planar back with at least three sides extending upwardly from the peripheral edges of the back;
- a lid forming a front on the pack, said lid being attached along a portion of one end thereof to the bottom of the body, the lid having a flexible portion and being configured so as to have operable positions of at least a closed position, a partially open position, and a fully open position, the lid being foldable at at least one position along its width so as to place it in the partially open position, the pack occupying substantially the same amount of surface space as when the lid is in the partially open position as when the lid is in the closed position and user access to substantially all materials within the pack being permitted when the lid is in the partially open position;
- a connecting means for detachably securing the lid along its remaining edges to the sides of the pack;
- a plurality of exterior pockets located on the lid and sides of the pack;
- a plurality of drawer pockets located in the interior of the pack for securing and organizing equipment stored in the pack, at least one of the drawer pockets being attached to the lid and at least one of the drawer pockets being attached to the body, at least one of said drawer pockets attached to the body having an opening substantially adjacent to the foldable position of the lid so as to permit user access into that drawer pocket when the lid is in the partially open position, all of the drawer pockets being oriented in the same direction within the pack when the pack is completely closed such that the contents of all of the drawer pockets are accessible when the pack is in either the fully open or the partially open position, each drawer pocket comprising:
  - a first side generally rectangular in shape and being securely attached along one edge thereof to the body of the pack;
  - a second side generally rectangular in shape and being securely attached along one edge thereof to the body in a position substantially parallel to the first side;
  - fastening means along a distal edge of both the first and the second parallel sides, said fastening means being designed so as to secure the distal edge of the first side to the distal edge of the second side; and
  - a pouch located within each drawer pocket, each drawer pocket being formed as a receptacle for a corresponding pouch with at least one side of each drawer pocket being capable of being opened such that the pouch is removable from the drawer pocket, the pouch having a handle mounted to one end thereof for use in removing the pouch from the drawer pocket, the pouch providing storage for equipment such that the equipment stored in the pouch is accessible by opening the open drawer pocket when the pouch remains within the drawer pocket or by pulling on the handle to slide the pouch from the drawer pocket;
- a plurality of additional pockets located in the interior of the pack; and
- transporting means comprising handles whereby the pack can be carried by hand and shoulder straps such that the pack can be worn as a backpack.

* * * * *

UNITED STATES PATENT AND TRADEMARK OFFICE
CERTIFICATE OF CORRECTION

PATENT NO. : 4,609,084

DATED : September 2, 1986

INVENTOR(S) : Frank O. Thomas

It is certified that error appears in the above-identified patent and that said Letters Patent is hereby corrected as shown below:

Column 2, line 42, "half way" should be --halfway--
Column 3, line 7, "Another objection" should be --Another object--
Column 4, line 20, "of if" should be --or if--
Column 4, line 28, "pack 10 period." should be --pack 10.--
Column 5, line 60, "open position" should be --half open position--
Column 7, line 61, "Pocket 194" should be --Pocket 192--
Column 8, line 2, "sides walls 200" should be --side walls 200--
Column 8, line 31, "central characteristics" should be --essential characteristics--

Signed and Sealed this

Thirteenth Day of January, 1987

Attest:

DONALD J. QUIGG

Attesting Officer

Commissioner of Patents and Trademarks